(12) United States Patent
Aoki

(10) Patent No.: US 11,953,467 B2
(45) Date of Patent: Apr. 9, 2024

(54) GAS CONCENTRATION DETECTION DEVICE

(71) Applicant: DENSO CORPORATION, Kariya (JP)

(72) Inventor: Mitsuru Aoki, Kariya (JP)

(73) Assignee: DENSO CORPORATION, Kariya (JP)

( * ) Notice: Subject to any disclaimer, the term of this patent is extended or adjusted under 35 U.S.C. 154(b) by 422 days.

(21) Appl. No.: 17/403,601

(22) Filed: Aug. 16, 2021

(65) Prior Publication Data

US 2022/0057364 A1 Feb. 24, 2022

(30) Foreign Application Priority Data

Aug. 18, 2020 (JP) ................................ 2020-138191

(51) Int. Cl.
*G01N 27/626* (2021.01)
*G01N 33/00* (2006.01)
*H03M 1/56* (2006.01)

(52) U.S. Cl.
CPC ....... *G01N 27/626* (2013.01); *G01N 33/0027* (2013.01); *H03M 1/56* (2013.01)

(58) Field of Classification Search
CPC ............ G01N 27/626; G01N 33/0027; G01N 27/4067; G01N 27/407; H03M 1/56
See application file for complete search history.

(56) References Cited

U.S. PATENT DOCUMENTS

| | | | |
|---|---|---|---|
| 4,419,190 A | 12/1983 | Dietz et al. | |
| 6,336,354 B1 * | 1/2002 | Suzuki | G01N 27/4067 |
| | | | 338/34 |
| 6,870,142 B2 * | 3/2005 | Hada | F02D 41/1494 |
| | | | 219/494 |
| 7,288,175 B2 * | 10/2007 | Hada | G01N 27/4067 |
| | | | 73/23.31 |
| 9,769,877 B2 * | 9/2017 | Yazawa | H05B 1/0244 |
| 11,454,622 B2 * | 9/2022 | Billat | G01N 33/0031 |
| 11,686,695 B2 * | 6/2023 | Hedrich | G01N 25/18 |
| | | | 702/189 |
| 2002/0179443 A1 | 12/2002 | Hada et al. | |
| 2004/0045824 A1 | 3/2004 | Hada et al. | |
| 2007/0012565 A1 * | 1/2007 | Suzuki | G01N 27/124 |
| | | | 204/424 |
| 2015/0114848 A1 | 4/2015 | Engelke et al. | |
| 2019/0107505 A1 * | 4/2019 | Nunome | G01N 27/4065 |

FOREIGN PATENT DOCUMENTS

JP 2007-024538 A 2/2007

* cited by examiner

*Primary Examiner* — Freddie Kirkland, III
(74) *Attorney, Agent, or Firm* — POSZ LAW GROUP, PLC

(57) ABSTRACT

A gas concentration detection device includes: a gas concentration sensor having a gas sensor element that outputs an electric signal according to a gas concentration and a heater that heats the gas sensor element; a heater controller controlling energization and de-energization of the heater; a sensor controller having an ADC AD-converting the electric signal from an analog signal to a digital signal in synchronization with a sampling clock (fs) and detecting the gas concentration based on an output signal of the AD converter; and a timing adjuster shifting a switching timing of energization control from a conversion timing at which the AD converter performs the AD conversion.

14 Claims, 11 Drawing Sheets

GAS CONCENTRATION DETECTION DEVICE

CROSS REFERENCE TO RELATED APPLICATION

The present application is based on and claims the benefit of priority of Japanese Patent Application No. 2020-138191, filed on Aug. 18, 2020, the disclosure of which is incorporated herein by reference.

TECHNICAL FIELD

The present disclosure generally relates to a gas concentration detection device.

BACKGROUND ART

A gas concentration detection device performs moving average processing on sensor signals from gas sensors sampled at predetermined intervals in a microcomputer. By setting a range of the moving average to a natural number multiple of a pulse width modulation (PWM) control cycle of the heater, the sampling values calculated by the moving average are controlled to have the same number of (a) and (b), i.e., (a) sampling values including a first type of noise generated at a rising edge of the PWM control cycle, and (b) sampling values including a second type of noise generated at a falling edge of the PWM control cycle.

Since the first type of noise and the second type of noise appear in opposite directions, they might cancel out each other and the influence of noise can thus be suitably avoided.

However, the gas concentration detection device may possibly be not able to sufficiently avoid the influence of noise in the moving average processing of the sensor signal. Therefore, the gas concentration detection device is required to further improve the detection accuracy of the gas concentration.

The plurality of aspects/embodiments disclosed herein employ different technical means to achieve their respective objectives. Reference numerals in parentheses described in claims and this section exemplarily show corresponding relationships with parts of embodiments to be described later and are not intended to limit technical scopes of the disclosure. The objects, features, and advantages disclosed in the present specification will become apparent by referring to following detailed descriptions and accompanying drawings.

DETAILED DESCRIPTION

Figure 1:
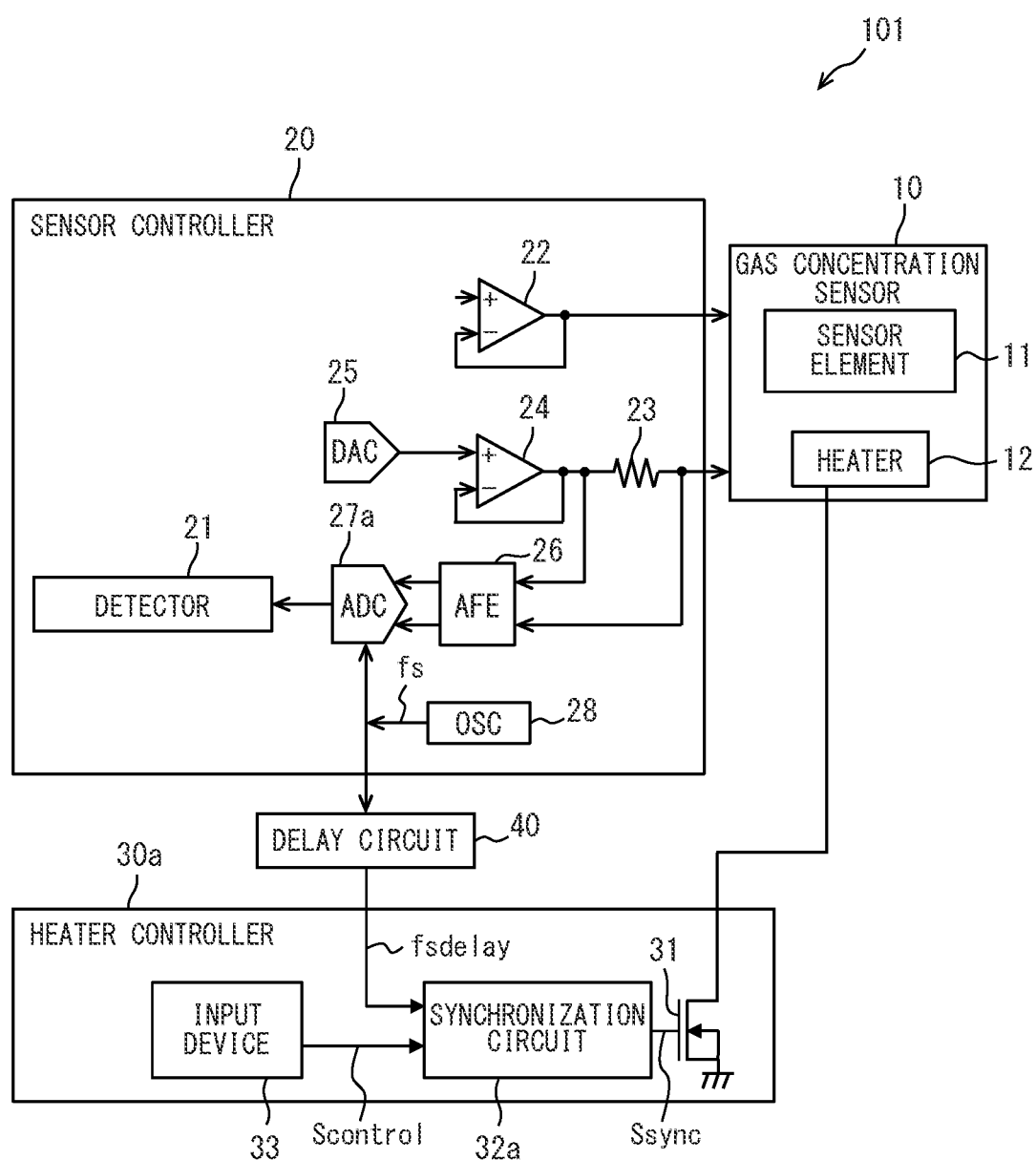
FIG. 1 is a block diagram of a schematic configuration of a gas concentration detection device according to a first embodiment.

Multiple embodiments for implementing the present disclosure are described with reference to the drawings. In each of the embodiments, portions corresponding to those described in the preceding embodiment are denoted by the same reference numerals, and redundant descriptions may be omitted in some cases. In each of the embodiments, in a case where only a part of the configuration is described, the other part of the configuration may be incorporated from the other, preceding embodiment(s).

Figure 2:
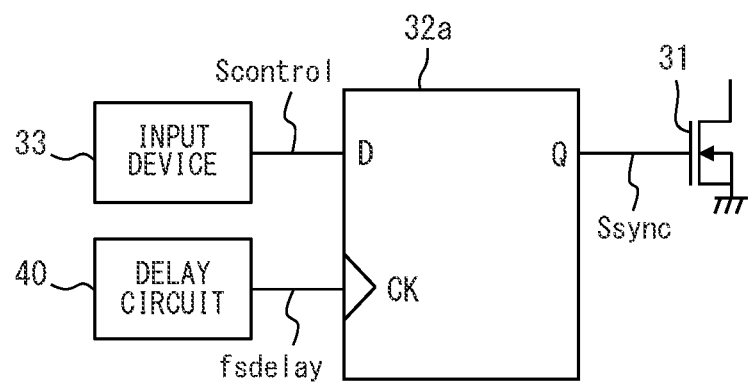
FIG. 2 is a block diagram of a schematic configuration of a synchronization circuit according to the first embodiment.
Figure 3:
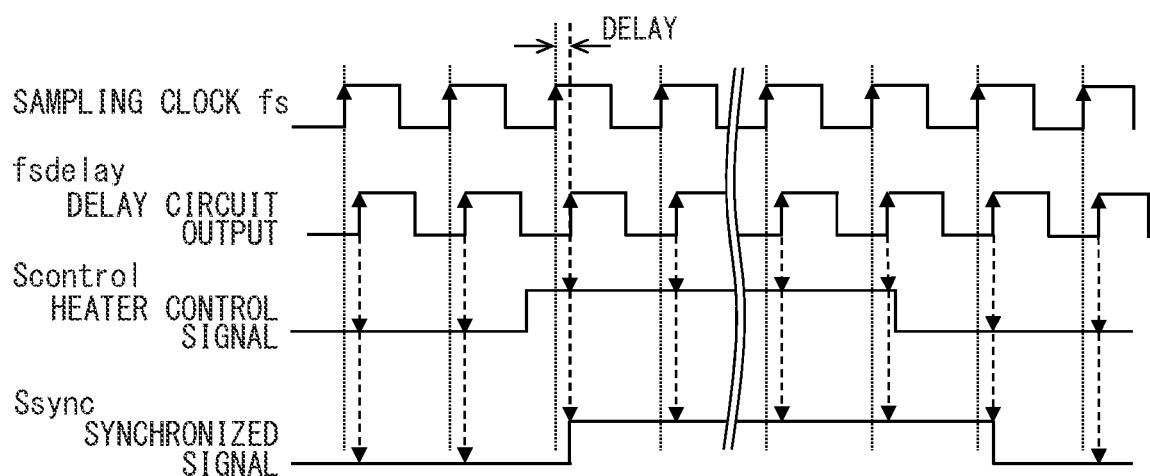
FIG. 3 is a timing chart of an operation of the gas concentration detection device according to the first embodiment.

First Embodiment, FIGS. 1-3

A gas concentration detection device 101 of the first embodiment is described with reference to FIGS. 1 to 3. The gas concentration detection device 101 includes a gas concentration sensor 10, a sensor controller 20, a heater controller 30*a*, a delay circuit 40, and the like.

The gas concentration sensor 10 includes a sensor element 11 and a heater 12. The gas concentration sensor 10 is arranged in an exhaust passage of an engine (e.g., an internal-combustion engine). The sensor element 11 contains a solid electrolyte. The sensor element 11 outputs a linear electric signal according to a specific component in an exhaust gas. In other words, the sensor element 11 outputs an electric signal according to a gas concentration. Specific components include oxygen concentration and unburned components such as CO, HC, and H2. The heater 12 heats the sensor element 11 (i.e., solid electrolyte body). As the gas concentration sensor 10, for example, a laminated/layered sensor in which the heater 12 is laminated/layered on the sensor element 11 can be adopted. The sensor element 11 corresponds to a gas sensor element.

The sensor controller 20 drives the gas concentration sensor 10 to detect the gas concentration. The sensor controller 20 includes, as its main components, a detector 21 and an analog-digital converter (ADC) 27*a*. Further, in the present embodiment, as an example, a sensor controller 20 including a first amplifier (AMP) 22, a resistance element 23, a second amplifier (AMP) 24, a digital-analog converter (DAC) 25, an AFE 26, and an oscillator 28 is adopted. The first AMP 22 and the DAC 25 are connected to, for example, a control logic circuit or the like. Further, the first AMP 22 is connected to a control logic circuit or the like via a DAC that is different from the DAC 25, for example.

The ADC (Analog-to-digital converter) 27a is an AD converter that AD-converts an analog signal to a digital signal. The AFE (Analog Front End) 26 is an analog circuit that amplifies or aligns the levels of electric signals output from the sensor element 11. The DAC (Digital-to-Analog Converter) 25 is a DA converter that DA-converts a digital signal to an analog signal.

The detector 21 is connected to the output terminal of the ADC 27a. The detector 21 detects the gas concentration based on the output signal of the ADC 27a. The detector 21 can be configured by, for example, a logic circuit or the like.

An output terminal of the first AMP 22 is connected to its own inverted input terminal and the gas concentration sensor 10. An output terminal of the DAC 25 is connected to a non-inverted input terminal of the second AMP 24. An output terminal of the second AMP 24 is connected to its own inverted input terminal, and is also connected to the gas concentration sensor 10 via the resistance element 23. The resistance element 23 is a shunt resistor.

An input terminal of the ADC 27a is a differential input. Input terminals of the ADC 27a are connected to output terminals of the AFE 26. An output terminal of the ADC 27a is connected to the detector 21.

The ADC 27a AD-converts the electric signal output by the sensor element 11 in synchronization with a sampling clock fs. As shown in FIG. 3, the ADC 27a performs AD conversion in synchronization with, for example, a rising edge of the sampling clock fs. It may also be understood that the ADC 27a AD-converts an electric current flowing through the sensor element 11 in synchronization with the sampling clock fs. Further, it may also be understood that the ADC 27a detects the electric current flowing through the sensor element 11.

The timing at which the ADC 27a performs AD conversion may be describable as an AD conversion timing or a data acquisition timing. On the other hand, the time during which the ADC 27a is performing AD conversion may be describable as an AD conversion time.

The oscillator (OSC) 28 is connected to the heater controller 30a via the ADC 27a and the delay circuit 40 described later. The oscillator 28 outputs the sampling clock fs.

The sensor controller 20 shown in FIG. 1 is only an example. That is, the sensor controller 20 of the present disclosure is not limited to the above configuration. The sensor controller 20 can be adopted as long as it has a configuration which includes an ADC 27a that AD-converts an electric signal output from the sensor element 11 in synchronization with the sampling clock fs for detecting the gas concentration based on the output signal of the ADC 27a.

The heater controller 30a includes a heater switch 31, a synchronization circuit 32a, an input device 33, and the like. The heater controller 30a controls energization and de-energization of the heater 12.

The heater switch 31 is adopted as a MOSFET (Metal-oxide semiconductor Field Effect Transistor) as an example. A gate terminal of the heater switch 31 is connected to the synchronization circuit 32a. A drain terminal of the heater switch 31 is connected to the heater 12. A source terminal of the heater switch 31 is connected to the ground. In the heater switch 31, a synchronization signal output from the synchronization circuit 32a is input to the gate terminal.

The heater switch 31 turns ON when the synchronization signal is turned ON, and turns OFF when the synchronization signal is turned OFF. The heater controller 30a energizes the heater 12 when the heater switch 31 is turned ON. Further, the heater controller 30a de-energizes the heater 12 when the heater switch 31 is turned OFF. The heater 12 is energized by duty ratio control.

The synchronization circuit 32a is connected to the input device 33, the delay circuit 40, and the gate terminal of the heater switch 31. As shown in FIG. 2, the synchronization circuit 32a is composed of a D flip-flop. In the synchronization circuit 32a, a delay circuit signal is input to a CK terminal from the delay circuit 40 described later. Further, in the synchronization circuit 32a, a heater control signal is input to a D terminal from the input device 33 described later. Then, the synchronization circuit 32a outputs a synchronization signal from a Q terminal.

That is, the synchronization circuit 32a outputs, from the Q terminal, a synchronization signal corresponding to the heater control signal that is input to the D terminal in synchronization with the delay circuit signal. The synchronization circuit 32a outputs a synchronization signal in synchronization with, for example, a rising edge of the delay circuit signal. Note that the synchronization circuit 32a outputs an H level signal as, for example, turning ON of the synchronization signal. Further, the synchronization circuit 32a outputs an L level signal as, for example, turning OFF of the synchronization signal.

The synchronization signal is a signal for switching between energization and de-energization of the heater 12. Therefore, the synchronization signal can be designated as a heater drive signal.

The input device 33 is connected to the synchronization circuit 32a. A control signal is input to the input device 33 from an electronic control device or the like provided outside the gas concentration detection device 101. The input device 33 outputs a heater control signal indicating energization and de-energization of the heater 12 based on the control signal. The input device 33 outputs, for example, an H level signal (1) as a heater control signal indicating energization of the heater 12. Further, the input device 33 outputs an L level signal as a heater control signal (0) indicating that the heater 12 is not energized, for example.

The delay circuit 40 is a circuit that delays the sampling clock fs output from the oscillator 29. The delay circuit 40 delays the sampling clock fs and outputs a delayed sampling clock fsdelay to the synchronization circuit 32a. The delayed sampling clock fsdelay may also be referred to as the delay circuit signal. The delay circuit 40 delays the sampling clock fs by an amount of time sufficiently longer than the AD conversion time.

Further, the synchronization circuit 32a and the delay circuit 40 correspond to a timing adjuster. Therefore, it may be understood that the gas concentration detection device 101 includes, as a timing adjuster, a synchronization circuit 32a and a delay circuit 40. As shown in FIG. 3, the timing adjuster is a component that shifts the switching timing of energization control from the conversion timing at which the ADC 27a performs AD conversion. Specifically, in FIG. 1 the input device 33 outputs a control signal Scontrol. The synchronization circuit 32a receives the delayed sampling clock fsdelay, receives the control signal Scontrol, and outputs a synchronization signal Ssync to the switch 31. The switch 31 may be switched ON to ground the heater 12, thus energizing the heater 12 by permitting current to pass through the heater.

That is, the timing adjuster shifts/delays the switching timing of the heater 12 energization relative to the conversion timing of the ADC 27a.

Note that the switching timing can be regarded as coinciding with an output timing of the synchronization signal Ssync. That is, the switching timing from de-energization to energization coincides with the output timing of the H level signal by the synchronization circuit 32a. The switching timing from energization to de-energization coincides with the output timing of the L level signal by the synchronization circuit 32a.

In FIG. 1, the delay circuit 40 delays the sampling clock fs and outputs the delayed sampling clock fsdelay (also knowns as a delay circuit signal). In FIG. 2, the synchronization circuit 32a is a D flip flop. The D flip flop receives the delay circuit signal fsdelay in the CK terminal, and receives the control signal Scontrol from the input device 33, and outputs the synchronized signal Ssync.

In FIG. 3, the synchronized signal Ssync changes from low to high at a time that is delayed (DELAY) relative to the sampling clock fs. Thus, the heater 12 does not begin energization at the same time that the analog digital converter 27a begins its conversion on the leading edge of the sampling clock fs. Note, the digital to analog converter 25 may also be controlled by the sampling clock fs.

<Effects>

As described above, the gas concentration detection device 101 includes a timing adjuster having the synchronization circuit 32a and the delay circuit 40. Therefore, the gas concentration detection device 101 does not perform AD conversion by the ADC 27c at the switching timing. Therefore, the gas concentration detection device 101 can suppress/prevent that the noise generated by the energization control of the heater 12 adversely affects the AD conversion performed by the ADC 27c. Therefore, the gas concentration detection device 101 can suppress deterioration in the detection accuracy of the gas concentration.

A preferred embodiment of the present disclosure has been described above. However, the present disclosure is not limited to the above embodiment, and various modifications are possible without departing from the spirit and scope of the present disclosure. Hereinafter, the second to fifth embodiments are described as other embodiments of the present disclosure. The above-described embodiment and the second to fifth embodiments can be carried out individually, but can also be carried out in combination as appropriate. The present disclosure can be performed by various combinations without being limited to the combination illustrated in the embodiments.

Figure 4:
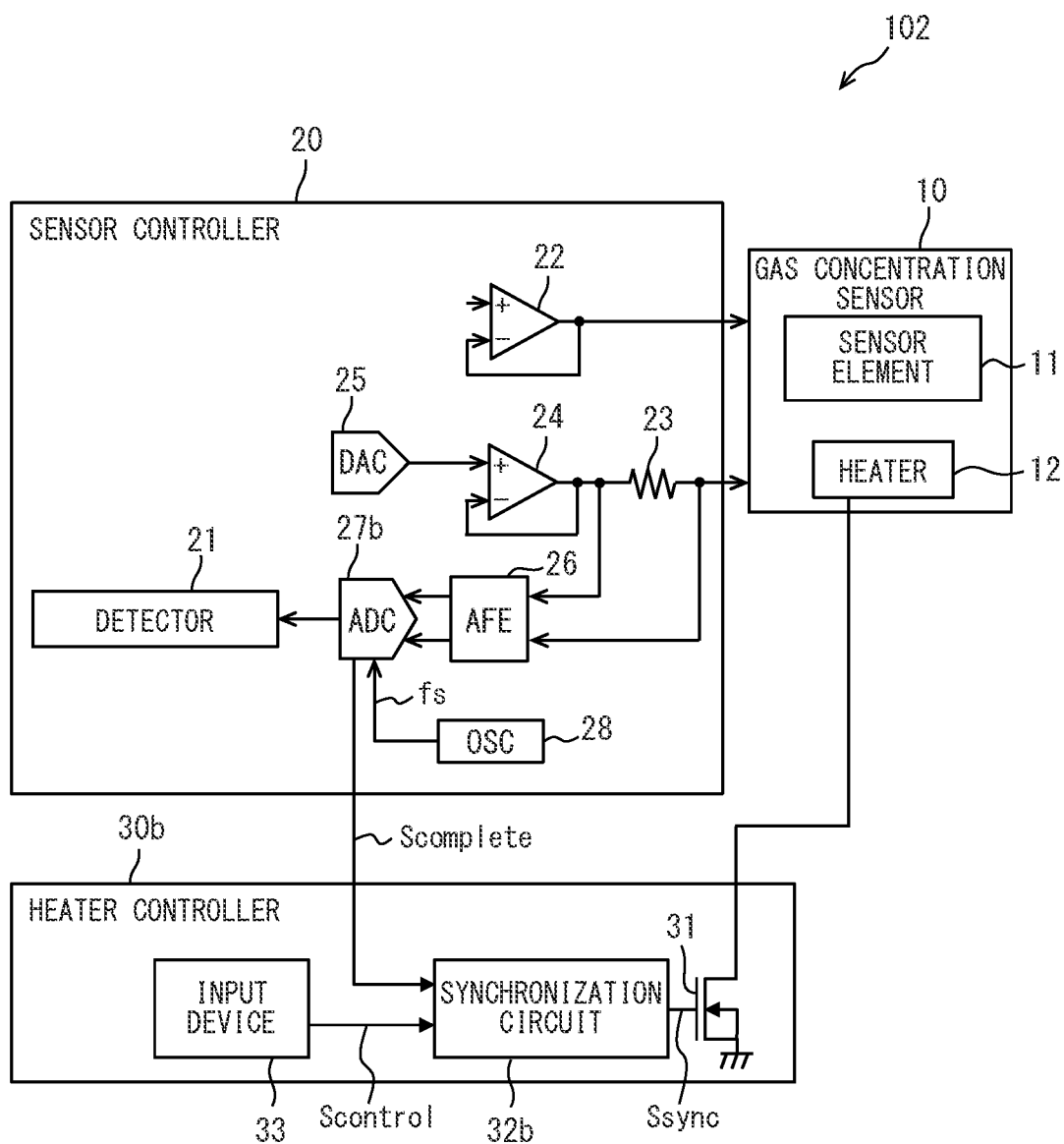
FIG. 4 is a block diagram of a schematic configuration of the gas concentration detection device according to a second embodiment.
Figure 5:
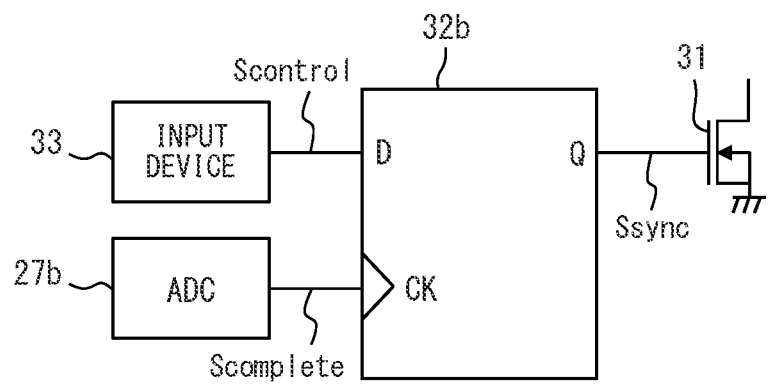
FIG. 5 is a block diagram of a schematic configuration of the synchronization circuit according to a second embodiment.
Figure 6:
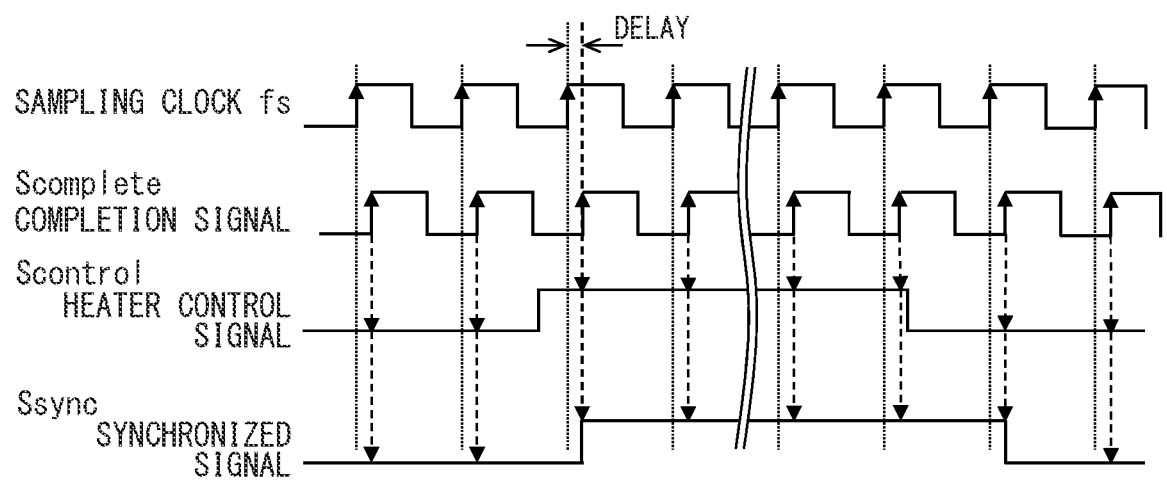
FIG. 6 is a timing chart of the operation of the gas concentration detection device according to the second embodiment.

Second Embodiment, FIGS. 4-6

A gas concentration detection device 102 of the second embodiment is described with reference to FIGS. 4, 5 and 6. The gas concentration detection device 102 is different from the gas concentration detection device 101 in the configuration of an ADC 27b and the synchronization circuit 32b. Further, it may also be understood that the gas concentration detection device 102 has a different timing adjuster configuration from the gas concentration detection device 101. The gas concentration detection device 102 has the same reference numerals assigned to the same configuration as the gas concentration detection device 101.

The ADC 27b performs AD conversion in the same manner as the ADC 27a, upon a rising edge of the sampling clock fs. Further, the ADC 27b outputs a completion signal Scomplete when the AD conversion is complete. The completion signal Scomplete is a signal indicating that the AD conversion is complete. The completion signal Scomplete is substantially equal to the delay circuit signal fsdelay of FIG. 1, except that the delay of the completion signal may be dependent upon the data being processed, and except that the delay of the completion signal is being caused incidentally by the ADC 27a without requiring an additional delay circuit.

In FIG. 5, by using this completion signal as a CK input into the D flip flop, the synchronization signal Ssync is effectively restricted from starting to energize the heater 12 at the same time that the As shown in FIG. 6, the ADC 27b outputs a completion signal in the same cycle as the sampling clock fs. The ADC 27b outputs a completion signal with a delay from the sampling clock fs by an amount of time required for AD conversion. In the present embodiment, the completion signal is output with a delay from the rising edge of the sampling clock fs.

As shown in FIGS. 4 and 5, the heater controller 30b includes the input device 33 and a synchronization circuit 32b. The synchronization circuit 32b is connected to the input device 33, the ADC 27b, and the gate terminal of the heater switch 31. The synchronization circuit 32b is composed of a D flip-flop. In the synchronization circuit 32b, the heater control signal is input to the D terminal as in the synchronization circuit 32a. Then, the synchronization circuit 32b outputs a synchronization signal from the Q terminal, similarly to the synchronization circuit 32a. However, in the synchronization circuit 32b, the completion signal output from the ADC 27b is input to the CK terminal.

The synchronization circuit 32b outputs, from the Q terminal, a synchronization signal corresponding to the heater control signal input to the D terminal in synchronization with the completion signal. That is, the synchronization circuit 32b performs energization control in synchronization with the completion signal. As described above, the completion signal is output with a delay from the rising edge of the sampling clock fs by an amount of time required for AD conversion. Therefore, the synchronization circuit 32b outputs the synchronization signal after completion of the AD conversion. The ADC 27b and the synchronization circuit 32b correspond to a timing adjuster.

In such manner, the timing adjuster shifts the switching timing of the heater 12 from de-energization to energization from the conversion timing of the ADC 27a. Further, the timing adjuster delays/shifts the switching timing of the heater 12 relative to the conversion timing of the ADC 27a.

The gas concentration detection device 102 can exert the same effects as the gas concentration detection device 101.

Figure 7:
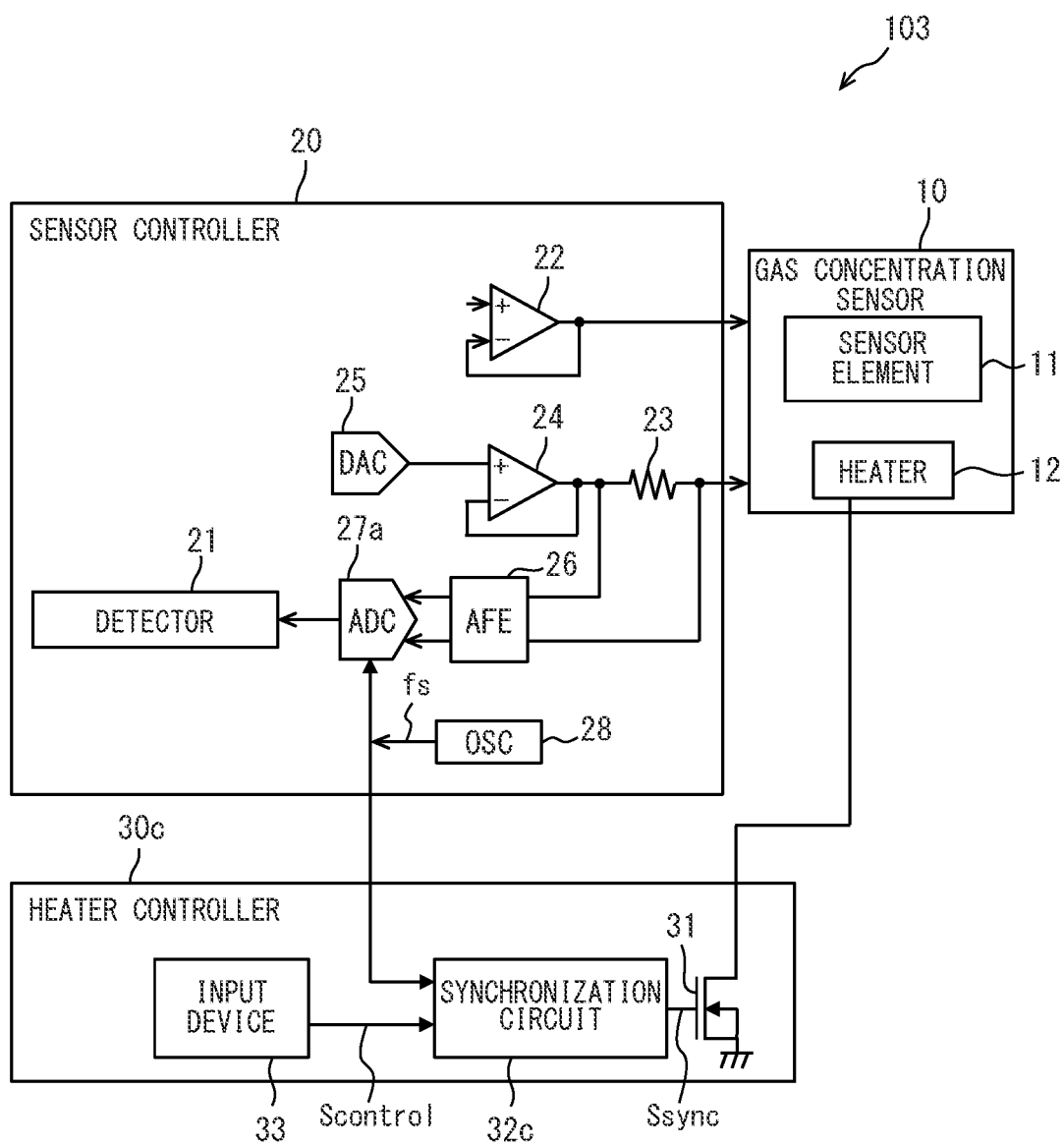
FIG. 7 is a block diagram of a schematic configuration of the gas concentration detection device according to a third embodiment.
Figure 8:
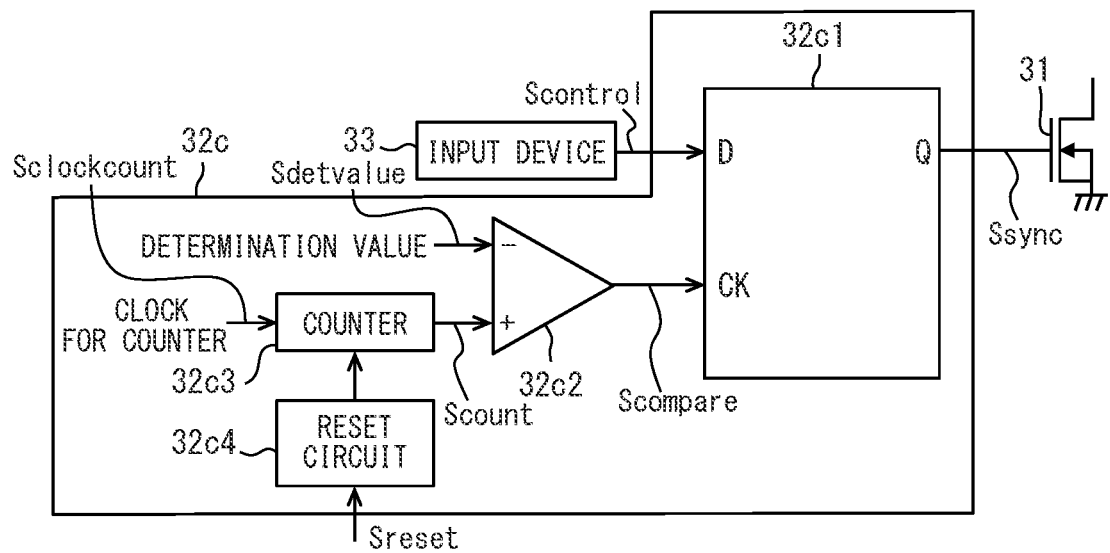
FIG. 8 is a block diagram of a schematic configuration of the synchronization circuit according to the third embodiment.
Figure 9:
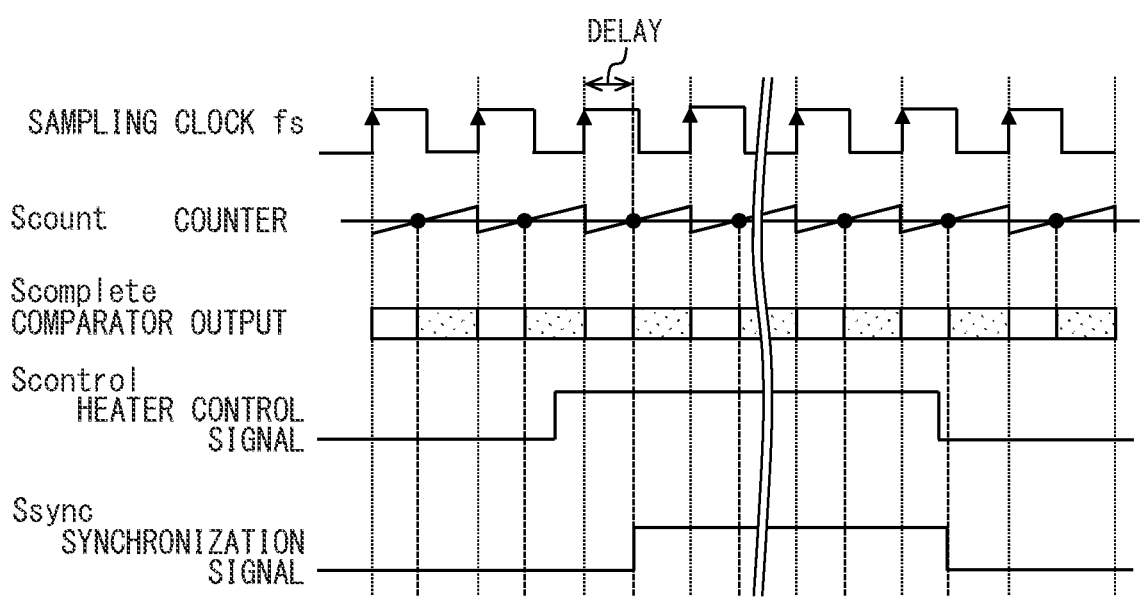
FIG. 9 is a timing chart of the operation of the gas concentration detection device according to the third embodiment.

Third Embodiment, FIGS. 7-9

A gas concentration detection device 103 of the third embodiment is described with reference to FIGS. 7, 8 and 9. The gas concentration detection device 103 is different from the gas concentration detection device 101 in the configuration of a synchronization circuit 32c. Further, it may also be understood that the gas concentration detection device 103 has a different timing adjuster configuration from the gas concentration detection device 101. The gas concentration detection device 103 has the same reference numerals assigned to the same configuration as the gas concentration detection device 101. FIG. 7 is very similar to FIG. 1, except that the delay circuit 40 is omitted from FIG. 7. The synchronization circuit 32c in FIG. 7 uses a counter to create a delay, as shown in FIGS. 8 and 9 discussed below. In FIG. 8, the determination value Sdetvalue is a threshold value input into a (−) input of the comparator 32c2. A counter 32c3 is (i) incremented by a clock for the counter Sclockcount, (ii) reset by the reset circuit 32c4 receiving a reset signal Sreset, and (iii) outputs a count value Scount to the (+) input terminal of the comparator S32c2. Note that the count value Scount is an analog signal. Thus, the counter 32c3 may include a DAC converter. In FIG. 8, the rising edge (on timing) of the synchronized signal Ssync is delayed (DELAY) relative to the rising edge of the sample clock fs (while the heater control signal Scontrol from the input device 33 into the D input of the D flip flop 32c1 is high.

As shown in FIGS. 7 and 8, a heater controller 30c includes the input device 33 and the synchronization circuit 32c. The synchronization circuit 32c includes a D-latch circuit 32c1, a comparator 32c2, a counter 32c3, and a reset circuit 32c4. The synchronization circuit 32c corresponds to a timing adjuster.

In the D-latch circuit 32c1, the input device 33 is connected to the D terminal, and the output terminal of the comparator 32c2 is connected to the CK terminal. The D-latch circuit 32c1 outputs a synchronization signal from the Q terminal.

A determination value and a count value are input to the comparator 32c2. The determination value is set based on a noise generation period nop. The electric current (i.e., heater current) flowing through the heater 12 starts to flow after the synchronization signal is output, and rises to a certain constant current value. During a nop period from the start of the flow of electric current to the constant current value, noise that adversely affects the AD conversion by the ADC 27a may occur. Therefore, this period of nop can be designated as the noise generation period nop. The noise generation period nop can be obtained by experiments, simulations, and the like. The determination value is set so that the conversion timing does not occur during the noise generation period nop.

A clock for the counter is input to the counter 32c3. The counter 32c3 counts the clock for the counter and outputs a count value to the comparator 32c2. The counter 32c3 resets the count value when a reset signal described later is input. Therefore, the counter 32c3 corresponds to a measurement unit that measures the time within one cycle of the sampling clock fs.

The reset circuit 32c4 outputs a reset signal to the counter 32c3 in synchronization with the sampling clock fs. For example, the reset circuit 32c4 outputs a reset signal in synchronization with the rising edge of the sampling clock fs.

The comparator 32c2 outputs a signal generated by the count value and the determination value. The comparator 32c2 inputs a signal to the CK terminal of the D-latch circuit 32c1. As shown in FIG. 9, a signal output by the comparator 32c2 is a periodic signal indicating an output period of the heater control signal and a mask period for masking the heater control signal. In FIG. 9, the output period is shown in white, and the mask period is hatched.

As shown in FIG. 9, when the count value is equal to or less than the determination value, the comparator 32c2 outputs a periodic signal indicating an output period. The output period is a permission period for permitting energization control. In such manner, the comparator 32c2 sets the output period when there is a predetermined amount of time from the measurement result of the counter 32c3 to the conversion timing. That is, the comparator 32c2 sets the output period corresponding to a permission period when there is a sufficient amount of time reservable before the conversion timing. Further, it may also be understood that the output period is set when the noise generation period nop and the conversion timing do not overlap.

As shown in FIG. 9, the comparator 32c2 outputs a periodic signal indicating a mask period when the count value exceeds the determination value. The mask period is a period during which energization control is prohibited. In such manner, the comparator 32c2 sets the mask period when there is not a predetermined amount of time from the measurement result of the counter 32c3 to the conversion timing. That is, the comparator 32c2 sets the mask period when there is not enough time before the conversion timing. Further, it may also be understood that the mask period is set when the noise generation period nop and the conversion timing overlap.

In such manner, the timing adjuster shifts the switching timing of the heater 12 from de-energization to energization from the conversion timing of the ADC 27a. Further, the timing adjuster delays/shifts the switching timing of the heater 12 relative to the conversion timing of the ADC 27a.

The gas concentration detection device 103 can exert the same effects as the gas concentration detection device 101.

Figure 10:
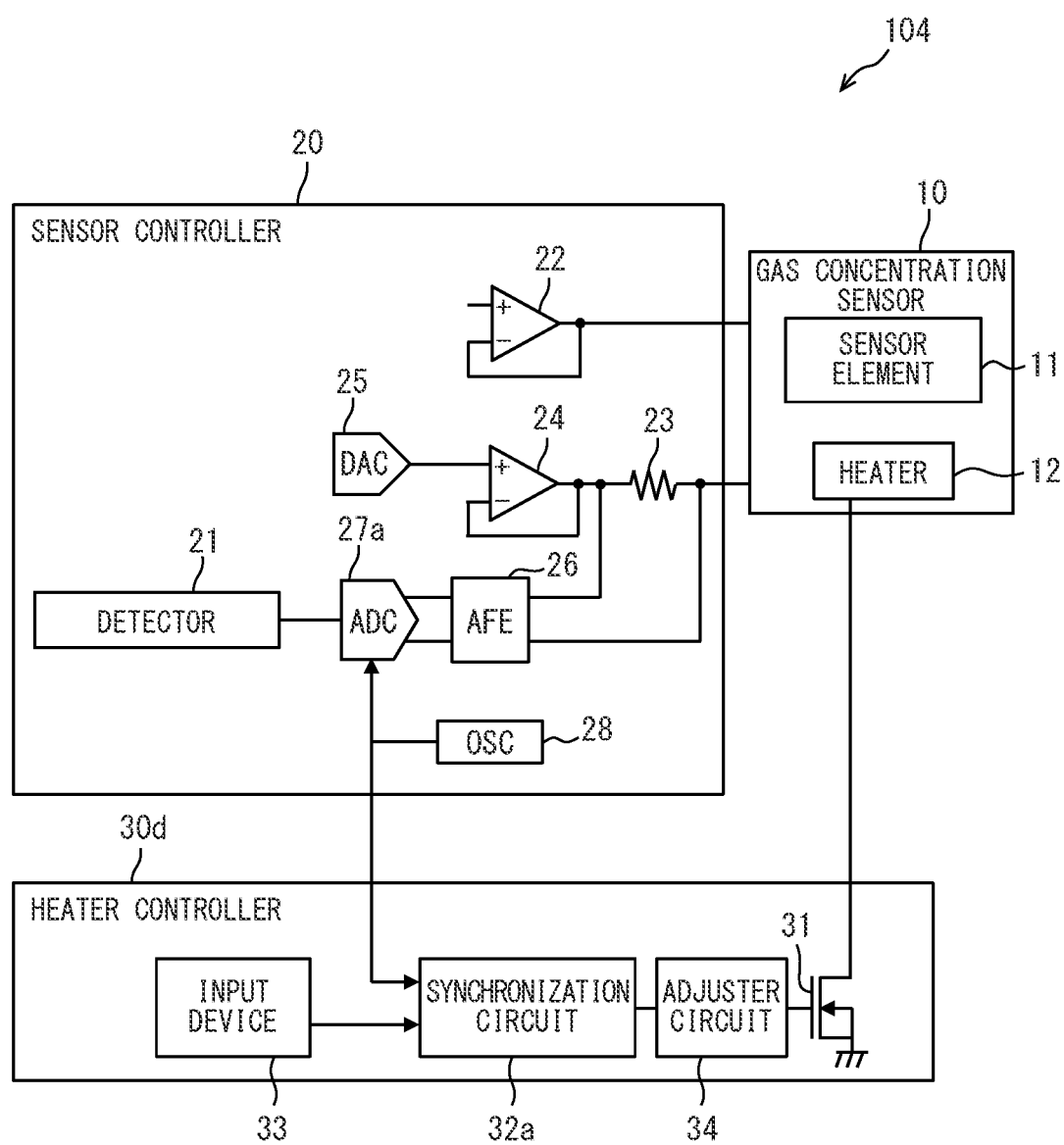
FIG. 10 is a block diagram of a schematic configuration of the gas concentration detection device according to a fourth embodiment.
Figure 11:
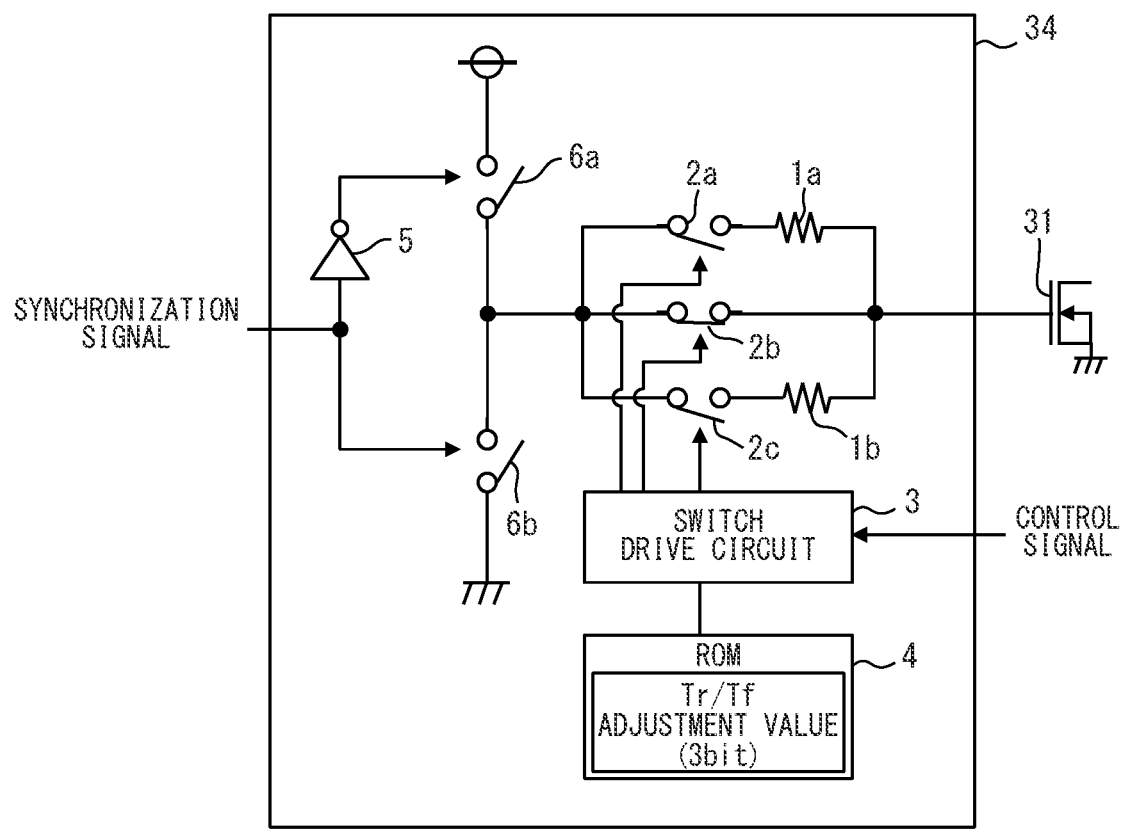
FIG. 11 is a block diagram of a schematic configuration of an adjuster circuit according to the fourth embodiment.
Figure 12:
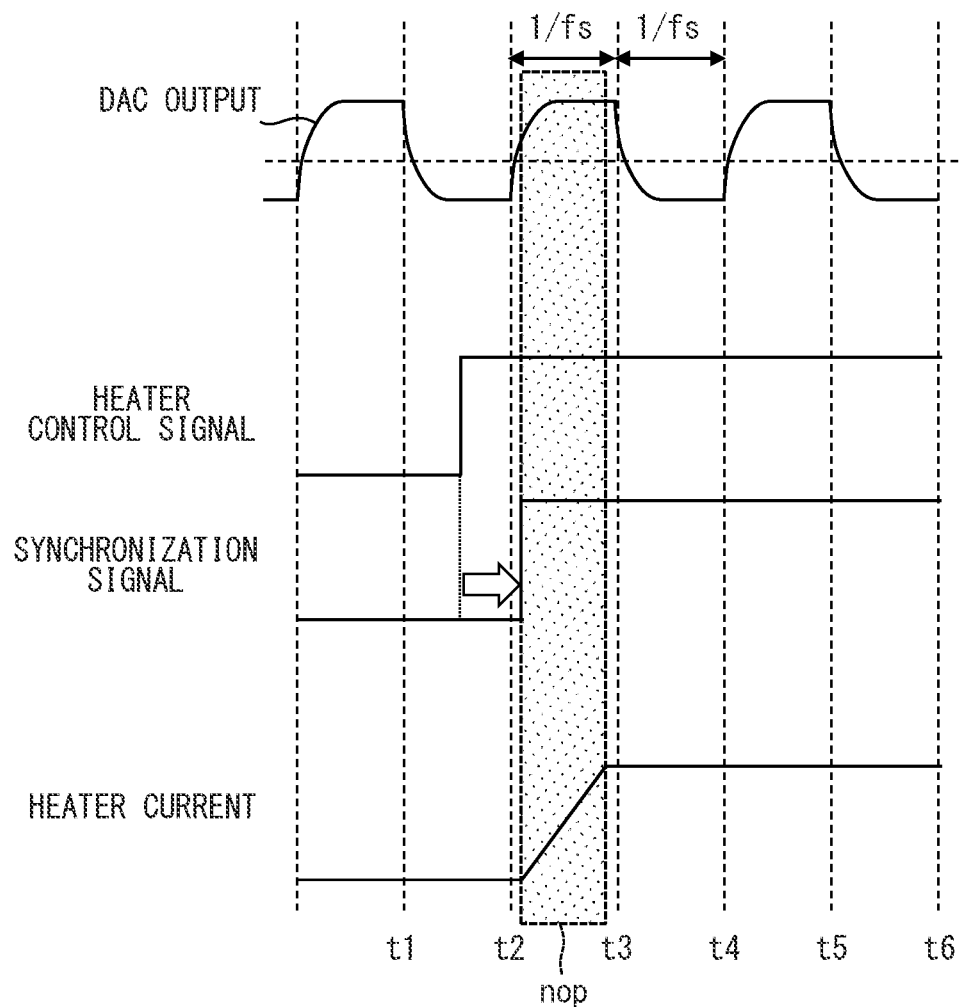
FIG. 12 is a timing chart of a noise generation period of the gas concentration detection device according to the fourth embodiment.

Fourth Embodiment, FIGS. 10-12

A gas concentration detection device 104 of the fourth embodiment is described with reference to FIGS. 10, 11, and 12. The gas concentration detection device 104 differs from the gas concentration detection device 101 in the configuration of a heater controller 30d. Further, it may also be understood that the configuration of the timing adjuster of the gas concentration detection device 104 is different from that of the gas concentration detection device 101. The gas concentration detection device 104 has the same reference numerals assigned to the same configuration as the gas concentration detection device 101.

As shown in FIGS. 10 and 11, the heater controller 30d includes the input device 33, the synchronization circuit 32a, and an adjuster circuit 34. The heater controller 30d includes the adjuster circuit 34 as a timing adjuster. The adjuster circuit 34 corresponds to an energization time adjuster circuit. Further, the heater controller 30d performs energization control by switching ON and OFF of the heater switch 31 electrically connected to the heater 12. The heater switch 31 corresponds to a semiconductor switch.

The adjuster circuit 34 is a circuit that adjusts a Tr time of the heater switch 31 and a Tf time of the heater switch 31. The Tr time is a rise time when the MOSFET of the heater switch 31 is turned ON. In other words, the Tr time can be designated as an energization time that transitions a de-energization state of the heater 12 to an energization state of the heater 12. The Tf time is a fall time when the MOSFET of the heater switch 31 is turned OFF. In other words, the Tf time can be designated as a de-energization time that transitions the energization state of the heater 12 to the de-energization state of the heater 12.

In order to turn ON/OFF the MOSFET which is the heater switch 31, a charge-discharge time of the MOSFET for charging/discharging a gate-source capacity and a drain-gate capacity is controlled. Then, the adjuster circuit 34 adjusts the Tr time and the Tf time by increasing or decreasing the charge/discharge current for such capacity. In particular, the adjuster circuit 34 adjusts the Tr/Tf time with a plurality of resistors.

Note that, in the present embodiment, an example of adjusting both of the Tr time and the Tf time is adopted. However, the present disclosure is not limited to such configuration, and any device that adjusts at least one of the Tr time and the Tf time can be adopted.

As shown in FIG. 11, the adjuster circuit 34 includes a NOT circuit 5, a first input switch 6a, and a second input switch 6b in an input stage. The first input switch 6a and the second input switch 6b are connected in series to a position between a power source and the ground. The first input switch 6a and the second input switch 6b are turned ON and OFF according to the synchronization signal. A synchronization signal is input to the first input switch 6a via the NOT circuit 5. A synchronization signal is input to the second input switch 6b without going through the NOT circuit 5.

The adjuster circuit 34 includes a first resistance element 1a, a second resistance element 1b, a first output switch 2a, a second output switch 2b, and a third output switch 2c in an output stage. The first resistance element 1a constitutes a series circuit with the first output switch 2a. The second resistance element 1b constitutes a series circuit with the third output switch 2c. These series circuits form a parallel circuit with the second output switch 2b. Further, this parallel circuit is provided at a position between (i) a connection point of the first input switch 6a and the second input switch 6b and (ii) a gate terminal of the heater switch 31.

Note that a series circuit of the first resistance element 1a and the first output switch 2a may also be referred to as a first path. The second resistance element 1b may also be referred to as a second path. A series circuit of the second resistance element 1b and the third output switch 2c may be referred to as a third path.

As the first resistance element 1a and the second resistance element 1b, those having different resistance values are adopted. For example, the resistance value of the second resistance element 1b may be twice the resistance value of the first resistance element 1a.

Further, the adjuster circuit 34 includes a switch drive circuit 3 that performs ON-OFF drive of the first output switch 2a, the second output switch 2b, and the third output switch 2c. Further, the adjuster circuit 34 includes a ROM 4 in which a Tr/Tf adjustment value is stored. The switch drive circuit 3 performs ON-OFF drive of the first output switch 2a, the second output switch 2b, and the third output switch 2c based on (i) a control signal from an electronic control device or the like provided outside the gas concentration detection device 104 and (ii) the Tr/Tf adjustment value. The Tr/Tf adjustment value is a value indicating which of the first output switch 2a, the second output switch 2b, and the third output switch 2c is turned ON.

Further, the switch drive circuit 3 selects a resistance value to be connected to the gate terminal by performing ON-OFF drive of the first output switch 2a, the second output switch 2b, and the third output switch 2c according to the Tr/Tf adjustment value. That is, the switch drive circuit 3 selects one of the first to third paths. The switch drive circuit 3 selects a path to limit the electric current that flows when the heater switch 31 is turned ON and the electric current that flows when the heater switch 31 is turned OFF. Further, it may also be understood that the adjuster circuit 34 has a plurality of resistance elements 1a and 1b at a position between the heater switch 31 and the adjuster circuit 34, and adjusts the energization time and the de-energization time by selecting which of the resistance elements 1a and 1b is used.

For example, when performing a control that decreases the Tr time, the switch drive circuit 3 selects, for example, the second path according to the Tr/Tf adjustment value, and reduces the resistance value connected to the gate terminal. Further, when performing a control that increases the Tr time, the switch drive circuit 3 selects, for example, the third path according to the Tr/Tf adjustment value, and increases the resistance value connected to the gate terminal.

By adjusting the Tr time, the adjuster circuit 34 completes transition from the de-energization state to the energization state in a period shorter than one cycle of the sampling clock fs. Further, by adjusting the Tf time, the adjuster circuit 34 completes transition from the energization state to the de-energization state in a period shorter than one cycle of the sampling clock fs. In such manner, the adjuster circuit 34 shifts the switching timing from the conversion timing. By adjusting the Tr time, the adjuster circuit 34 shifts the switching timing at the start of energization of the heater 12 from the conversion timing. Further, by adjusting the Tf time, the adjuster circuit 34 shifts the switching timing at the start of de-energization of the heater 12 from the conversion timing. It should be noted that the present disclosure can be adopted even in an adjuster circuit that performs at least only one of these adjustments.

For example, FIG. 12 shows a timing chart at the start of energization of the heater 12. Each of timings t1 to t6 indicates a rising edge of the sampling clock fs. Therefore, the ADC 27a performs AD conversion at each of timings t1 to t6.

The electric current (i.e., heater current) flowing through the heater 12 starts to flow after the synchronization signal is output, and rises to a certain constant current value. The period from the start of flow to the constant current value is the noise generation period nop. Then, the adjuster circuit 34 adjusts the noise generation period nop at the start of energization of the heater 12 by adjusting the Tr time. The adjuster circuit 34 adjusts the noise generation period nop at the start of de-energization of the heater 12 by adjusting the Tf time.

The gas concentration detection device 104 can exert the same effects as the gas concentration detection device 101.

Figure 13:
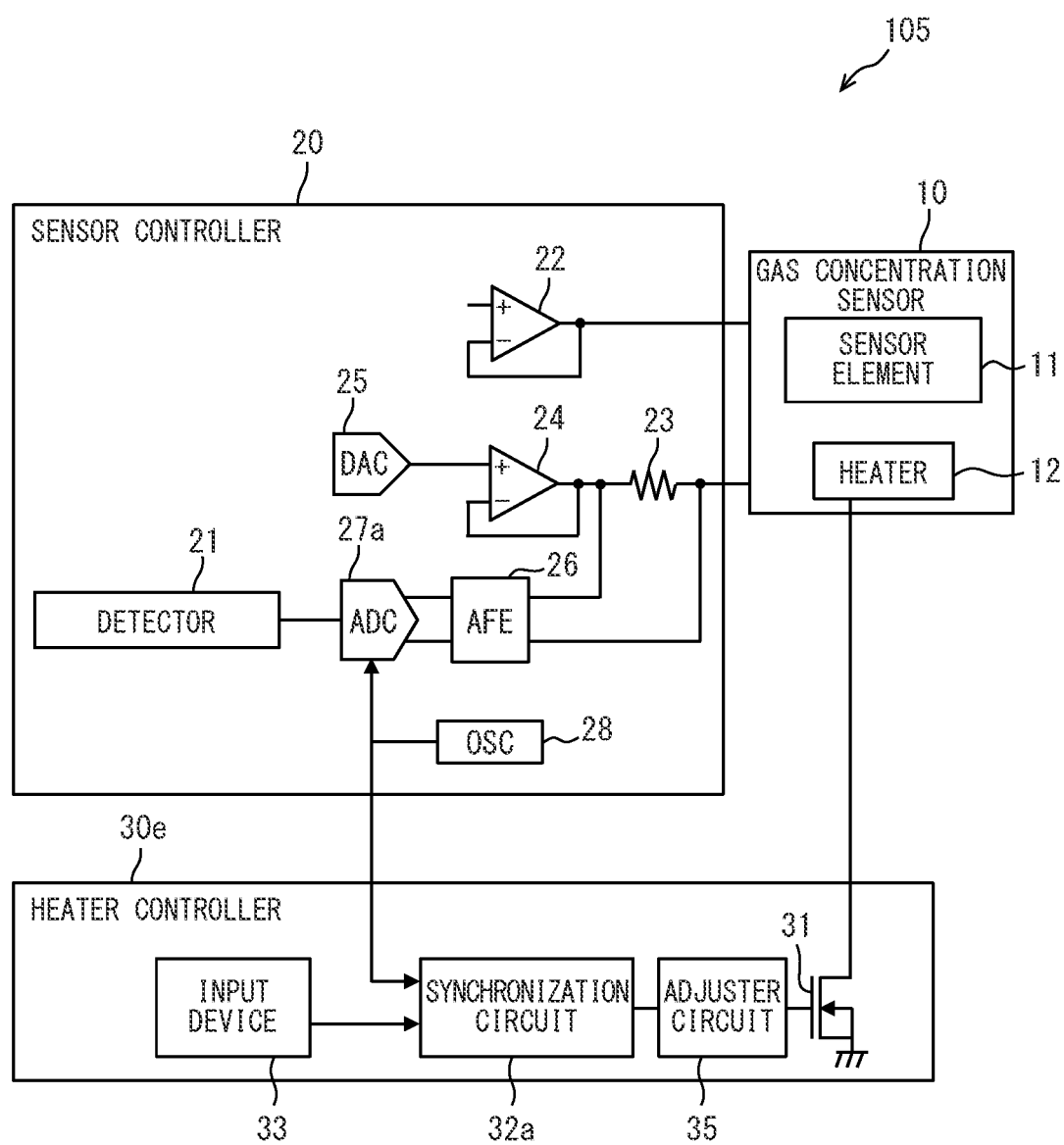
FIG. 13 is a block diagram of a schematic configuration of the gas concentration detection device according to a fifth embodiment.
Figure 14:
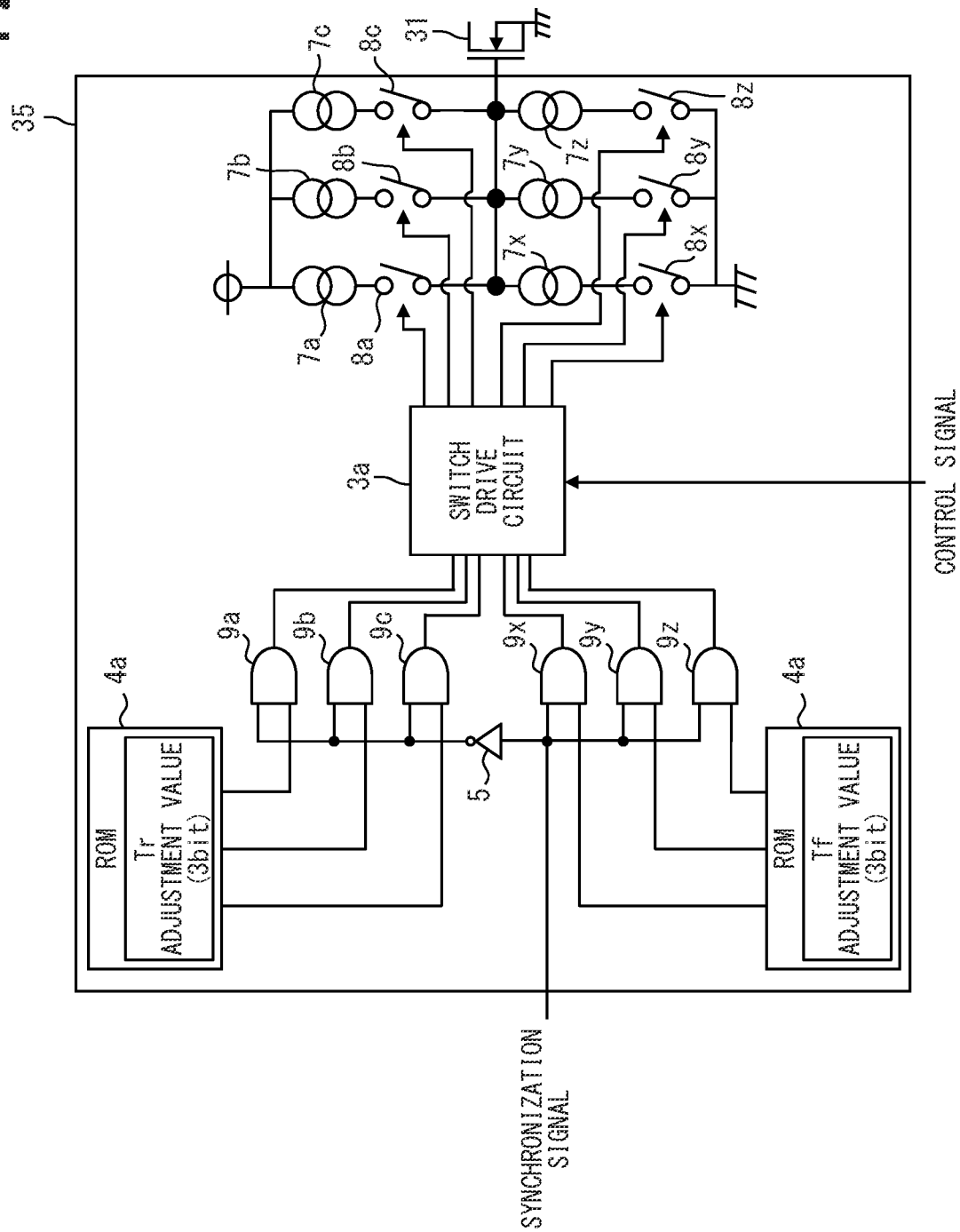
FIG. 14 is a block diagram of a schematic configuration of an adjuster circuit according to the fifth embodiment.

Fifth Embodiment, FIGS. 13 and 14

A gas concentration detection device 105 of the fifth embodiment is described with reference to FIGS. 13 and 14. The configuration of a heater controller 30e of the gas concentration detection device 105 is different from that of the gas concentration detection device 104. Further, it may also be understood that the configuration of the timing adjuster of the gas concentration detection device 105 is different from that of the gas concentration detection device 104. Further, the gas concentration detection device 105 is different from the gas concentration detection device 104 in that the energization time and the de-energization time are adjusted by a constant current circuit. The gas concentration detection device 105 has the same reference numerals assigned to the same configuration as the gas concentration detection device 104.

As shown in FIGS. 13 and 14, the heater controller 30e includes the input device 33, the synchronization circuit 32a, and an adjuster circuit 35. The adjuster circuit 35 corresponds to the energization time adjuster circuit. The adjuster circuit 35 includes a switch drive circuit 3a, a ROM 4a, and the NOT circuit 5.

The adjuster circuit 35 includes a first AND circuit 9a, a second AND circuit 9b, and a third AND circuit 9c for adjusting the Tr time in the input stage. Further, the adjuster circuit 35 includes a fourth AND circuit 9x, a fifth AND circuit 9y, and a sixth AND circuit 9z for adjusting the Tf time in the input stage.

Further, the adjuster circuit 35 includes a first constant current circuit 7a, a second constant current circuit 7b, and a third constant current circuit 7c for adjusting the Tr time in the output stage. The adjuster circuit 35 includes a first output switch 8a, a second output switch 8b, and a third output switch 8c connected respectively to the constant current circuits 7a to 7c.

Further, the adjuster circuit 35 includes a fourth constant current circuit 7x, a fifth constant current circuit 7y, and a sixth constant current circuit 7z for adjusting the Tf time in the output stage. The adjuster circuit 35 includes a fourth output switch 8x, a fifth output switch 8y, and a sixth output switch 8z connected respectively to the constant current circuits 7x to 7z.

The ROM 4a stores a Tr adjustment value and a Tf adjustment value. When the heater switch 31 is turned ON, the switch drive circuit 3a performs ON-OFF drive of the first output switch 8a, the second output switch 8b, and the third output switch 8c based on the control signal and the Tr adjustment value. In such manner, the switch drive circuit 3a selectively sets a constant current circuit when the heater switch 31 is turned ON from among the first constant current circuit 7a, the second constant current circuit 7b, and the third constant current circuit 7c. Note that the control signal is output from an electronic control device or the like provided outside the gas concentration detection device 105.

For example, when performing a control to decrease the Tr time, the switch drive circuit 3 controls the Tr adjustment value to increase the constant current circuit connected to the gate terminal, by turning ON all of the first output switch 8a to the third output switch 8c, for example. Further, when increasing the Tr time, the switch drive circuit 3 controls the Tr/Tf adjustment value to reduce the constant current circuit connected to the gate terminal, by turning ON of only the first output switch 8a, for example.

Further, when turning OFF the heater switch 31, the switch drive circuit 3a performs ON-OFF drive of the fourth output switch 8x, the fifth output switch 8y, and the sixth output switch 8z based on the control signal and the Tf adjustment value. In such manner, the switch drive circuit 3a selectively sets the constant current circuit when the heater switch 31 is turned OFF from among the fourth constant current circuit 7x, the fifth constant current circuit 7y, and the sixth constant current circuit 7z.

By adjusting the Tr time, the adjuster circuit 35 completes transition from the de-energization state to the energization state in a period shorter than one cycle of the sampling clock fs. Further, by adjusting the Tf time, the adjuster circuit 35 completes transition from the energization state to the de-energization state in a period shorter than one cycle of the sampling clock fs. In such manner, the adjuster circuit 35 delays/shifts the switching timing relative to the conversion timing. That is, the adjuster circuit 35 delays/shifts the switching timing at the start of energization of the heater 12 relative to the conversion timing by adjusting the Tr time. Further, by adjusting the Tf time, the adjuster circuit 34 shifts the switching timing at the start of de-energization of the heater 12 from the conversion timing. It should be noted that the present disclosure can be adopted even in an adjuster circuit that performs at least only one of these adjustments.

The gas concentration detection device 105 can exert the same effects as the gas concentration detection device 104.

Although the present disclosure has been described in accordance with the embodiments, it is understood that the present disclosure is not limited to such embodiments or structures. The present disclosure incorporates/encompasses various modifications and variations within the scope of equivalents. In addition, even though various combinations and forms are shown in the present disclosure, other combinations and forms, including only one element, added thereto or subtracted therefrom, are also considered to be within the scope and idea of the present disclosure.

What is claimed is:

1. A gas concentration detection device comprising:
   a gas concentration sensor having a gas sensor element that outputs an electric signal according to a gas concentration and a heater that heats the gas sensor element;
   a heater controller controlling energization and de-energization of the heater;
   a sensor controller having an AD converter AD-converting the electric signal from an analog signal to a digital signal in synchronization with a sampling clock and detecting the gas concentration based on an output signal of the AD converter; and
   a timing adjuster shifting a switching timing of energization control from a conversion timing at which the AD converter performs the AD conversion.

2. The gas concentration detection device of claim 1, wherein
   the timing adjuster includes a delay circuit for delaying the sampling clock and a synchronization circuit provided in the heater controller for inputting a delayed clock generated via the delay circuit, and
   the switching timing is shifted from the conversion timing by the synchronization circuit performing the energization control in synchronization with the delayed clock.

3. The gas concentration detection device of claim 1, wherein:
   the AD converter outputs a completion signal when the AD conversion is complete,
   the timing adjuster includes a synchronization circuit provided in the heater controller to which the completion signal is input, and
   the synchronization circuit performs the energization control in synchronization with the completion signal to shift the switching timing from the conversion timing.

4. The gas concentration detection device of claim 1, wherein
   the heater controller has a measurement unit that measures time within one cycle of the sampling clock,
   the timing adjuster is provided in the heater controller, and is capable of setting a permission period for permitting the energization control and a mask period for prohibiting the energization control, (a) the permission period being set when a predetermined amount of time is reservable as a period from an output of a measurement result by the measurement unit to the conversion timing and (b) the mask period being set when the predetermined amount of time is not reservable as a period from the output of the measurement result by the measurement unit to the conversion timing.

5. The gas concentration detection device of claim 1, wherein the heater controller includes, as the timing adjuster, an energization time adjuster circuit that adjusts at least one of (i) an energization time which is brought about as an energization state transitioned from a de-energization state and (ii) a de-energization time brought about as the de-energization state transitioned from the energization state, and the energization time adjuster circuit shifts the switching timing from the conversion timing by completing (a) transition from the de-energization state to the energization state or (b) transition from the energization state to the de-energization state in a period shorter than one cycle of the sampling clock.

6. The gas concentration detection device of claim 5, wherein the heater controller performs energization control by turning ON and OFF a semiconductor switch electrically connected to the heater, and the energization time adjuster circuit has a plurality of resistance elements at a position between itself and the semiconductor switch, and completes, in a period shorter than one cycle of the sampling clock, the transition from the de-energization state to the energization state or the transition from the energization state to the de-energization state by adjusting the energization time and the de-energization time by selecting which of the plurality of resistance elements is used.

7. The gas concentration detection device of claim 5, wherein the heater controller performs energization control by turning ON and OFF a semiconductor switch electrically connected to the heater, and the energization time adjuster circuit has a plurality of constant current circuits at a position between itself and the semiconductor switch, and completes, in a period shorter than one cycle of the sampling clock, the transition from the de-energization state to the energization state or the transition from the energization state to the de-energization state by adjusting the energization time and the de-energization time by selecting which of the plurality of constant current circuits is used.

8. A gas concentration detection device comprising:

a gas concentration sensor having a gas sensor element that outputs an electric signal according to a gas concentration and a heater that heats the gas sensor element;

a heater controller controlling energization and de-energization of the heater;

a sensor controller having an AD converter AD-converting the electric signal from an analog signal to a digital signal in synchronization with a sampling clock and detecting the gas concentration based on an output signal of the AD converter;

a timing adjuster shifting a switching timing of energization control from a conversion timing at which the AD converter performs the AD conversion;

a first processor located in the heater controller;

a first non-transitory computer-readable storage medium located in the heater controller;

a second processor located in the sensor controller; and a second non-transitory computer-readable storage medium located in the sensor controller.

9. The gas concentration detection device of claim 8, wherein the timing adjuster includes a delay circuit for delaying the sampling clock and a synchronization circuit provided in the heater controller for inputting a delayed clock generated via the delay circuit, and the switching timing is shifted from the conversion timing by the synchronization circuit performing the energization control in synchronization with the delayed clock.

10. The gas concentration detection device of claim 8, wherein:

the AD converter outputs a completion signal when the AD conversion is complete, the timing adjuster includes a synchronization circuit provided in the heater controller to which the completion signal is input, and the synchronization circuit performs the energization control in synchronization with the completion signal to shift the switching timing from the conversion timing.

11. The gas concentration detection device of claim 8, wherein the heater controller has a measurement unit that measures time within one cycle of the sampling clock, the timing adjuster is provided in the heater controller, and is capable of setting a permission period for permitting the energization control and a mask period for prohibiting the energization control, (a) the permission period being set when a predetermined amount of time is reservable as a period from an output of a measurement result by the measurement unit to the conversion timing and (b) the mask period being set when the predetermined amount of time is not reservable as a period from the output of the measurement result by the measurement unit to the conversion timing.

12. The gas concentration detection device of claim 8, wherein the heater controller includes, as the timing adjuster, an energization time adjuster circuit that adjusts at least one of (i) an energization time which is brought about as an energization state transitioned from a de-energization state and (ii) a de-energization time brought about as the de-energization state transitioned from the energization state, and the energization time adjuster circuit shifts the switching timing from the conversion timing by completing (a) transition from the de-energization state to the energization state or (b) transition from the energization state to the de-energization state in a period shorter than one cycle of the sampling clock.

13. The gas concentration detection device of claim 12, wherein the heater controller performs energization control by turning ON and OFF a semiconductor switch electrically connected to the heater, and the energization time adjuster circuit has a plurality of resistance elements at a position between itself and the semiconductor switch, and completes, in a period shorter than one cycle of the sampling clock, the transition from the de-energization state to the energization state or the transition from the energization state to the de-energization state by adjusting the energization time and the de-energization time by selecting which of the plurality of resistance elements is used.

14. The gas concentration detection device of claim 12, wherein the heater controller performs energization control by turning ON and OFF a semiconductor switch electrically connected to the heater, and the energization time adjuster circuit has a plurality of constant current circuits at a position between itself and the semiconductor switch, and completes, in a period shorter than one cycle of the sampling clock, the transition from the de-energization state to the energization state or the transition from the energization state to the de-energization state by adjusting the energization time and the de-energization time by selecting which of the plurality of constant current circuits is used.

* * * * *